United States Patent
Al Hunaidy et al.

(10) Patent No.: US 12,098,122 B2
(45) Date of Patent: Sep. 24, 2024

(54) PRODUCTION OF ACETIC ACID THROUGH CRYOGENIC SEPARATION OF SYNGAS

(71) Applicants: Saudi Arabian Oil Company, Dhahran (SA); Korea Advanced Institute of Science and Technology, Daejeon (KR)

(72) Inventors: Ali Shakir Al Hunaidy, Dhahran (SA); Hasan Imran, Dhahran (SA); Hyungmuk Lim, Daejeon (KR); Kosan Roh, Daejeon (KR); Jay H. Lee, Daejeon (KR)

(73) Assignee: Saudi Arabian Oil Company, Dhahran (SA)

(*) Notice: Subject to any disclaimer, the term of this patent is extended or adjusted under 35 U.S.C. 154(b) by 313 days.

(21) Appl. No.: 17/206,350

(22) Filed: Mar. 19, 2021

(65) Prior Publication Data
US 2022/0298095 A1 Sep. 22, 2022

(51) Int. Cl.
| | | |
|---|---|---|
| C07C 51/12 | (2006.01) | |
| C07C 29/151 | (2006.01) | |
| C07C 31/04 | (2006.01) | |
| C07C 41/09 | (2006.01) | |
| C07C 43/04 | (2006.01) | |
| C07C 53/08 | (2006.01) | |
| F25J 1/00 | (2006.01) | |

(52) U.S. Cl.
CPC .......... *C07C 51/12* (2013.01); *C07C 29/1518* (2013.01); *C07C 41/09* (2013.01); *F25J 1/0022* (2013.01); *C07C 31/04* (2013.01); *C07C 43/043* (2013.01); *C07C 53/08* (2013.01); *F25J 2205/40* (2013.01); *F25J 2210/18* (2013.01); *F25J 2210/60* (2013.01); *F25J 2210/80* (2013.01); *F25J 2215/18* (2013.01); *F25J 2215/80* (2013.01)

(58) Field of Classification Search
USPC ........................................................ 562/519
See application file for complete search history.

(56) References Cited

U.S. PATENT DOCUMENTS

| | | | |
|---|---|---|---|
| 4,217,759 A | 8/1980 | Shenoy | |
| 5,728,871 A * | 3/1998 | Joensen | C07C 51/12 |
| | | | 562/519 |
| 5,763,654 A | 6/1998 | Jones et al. | |
| 5,832,747 A | 11/1998 | Bassett et al. | |
| 6,175,039 B1 | 1/2001 | Voss | |
| 6,191,175 B1 | 2/2001 | Haugaard et al. | |
| 6,232,352 B1 * | 5/2001 | Vidalin | C01B 3/50 |
| | | | 518/700 |
| 6,608,114 B1 | 8/2003 | Heydorn et al. | |
| 7,067,558 B2 | 6/2006 | Grobys et al. | |
| 7,906,559 B2 | 3/2011 | Olah et al. | |
| 8,394,983 B2 | 3/2013 | Ditzel et al. | |
| 8,440,729 B2 | 5/2013 | Olah et al. | |
| 8,541,630 B2 | 9/2013 | Guo et al. | |
| 8,697,759 B1 | 4/2014 | Olah et al. | |
| 8,703,075 B2 | 4/2014 | Scates | |
| 8,729,141 B2 | 5/2014 | Bae et al. | |
| 8,957,259 B2 | 2/2015 | Dagle | |
| 8,966,937 B2 | 3/2015 | Halk-Beraud et al. | |
| 9,090,543 B2 | 7/2015 | Schoedel et al. | |
| 9,376,360 B2 | 6/2016 | Ahlers et al. | |
| 10,252,909 B2 | 4/2019 | Lofberg et al. | |
| 2010/0251765 A1 | 10/2010 | McNeil et al. | |

FOREIGN PATENT DOCUMENTS

| | | |
|---|---|---|
| EP | 0324475 | 7/1989 |
| EP | 0483609 | 5/1992 |
| EP | 1683780 | 7/2006 |
| KR | 20070030889 | 3/2007 |
| WO | WO 2007014534 | 2/2007 |
| WO | WO 2017057085 | 11/2017 |

OTHER PUBLICATIONS

Jones, "The Cativa Process for the Manufacture Plant of Acetic Acid," Platinum Metals Rev., 2000, 44:94-105.
Luyben, "Design and Control of a Methanol Reactor/Column Process," Ind. Eng. Chem. Res., 2010, 49:6150-6163.
Leonzio, "State of art and perspectives about the production of methanol, dimethyl ether and syngas by carbon dioxide hydrogenation," Journal of CO2 Utilization, 2018, 27:326-354, 29 pages.
Olah et al., "Chemical recycling of carbon dioxide to methanol and dimethyl ether: from greenhouse gas to renewable, environmentally carbon neutral fuels and synthetic hydrocarbons," The Journal of organic chemistry, 2009, 74(2):487-498, 12 pages.
Yang et al., "Progress and perspectives in converting biogas to transportation fuels," Renewable and Sustainable Energy Reviews, 2014, 40:1133-1152, 20 pages.
SAIP Examination Report in SAIP Appln. No. 122430792, dated Jun. 12, 2023, 20 pages, with English Translation.

* cited by examiner

*Primary Examiner* — Ana Z Muresan
(74) *Attorney, Agent, or Firm* — Fish & Richardson P.C.

(57) ABSTRACT

A system and method for producing acetic acid, including dry reforming methane with carbon dioxide to give syngas, cryogenically separating carbon monoxide from the syngas giving a first stream including primarily carbon monoxide and a second stream including carbon monoxide and hydrogen. The method includes synthesizing methanol from the second stream via hydrogenation of carbon monoxide in the second stream, synthesizing dimethyl ether from the methanol, and generating acetic acid from the dimethyl ether and first-stream carbon monoxide.

13 Claims, 2 Drawing Sheets

PRODUCTION OF ACETIC ACID THROUGH CRYOGENIC SEPARATION OF SYNGAS

TECHNICAL FIELD

This disclosure relates to conversion of carbon dioxide and the production of acetic acid.

BACKGROUND

Carbon dioxide is the primary greenhouse gas emitted through human activities. Carbon dioxide ($CO_2$) may be generated in various industrial and chemical plant facilities. At such facilities, the utilization of $CO_2$ as a feedstock may reduce $CO_2$ emissions at the facility and therefore decrease the $CO_2$ footprint of the facility. The conversion of the greenhouse gas $CO_2$ into value-added feedstocks or products may be beneficial. The dry reforming of methane may utilize $CO_2$.

SUMMARY

An aspect relates to a method of producing acetic acid, including dry reforming methane ($CH_4$) with carbon dioxide ($CO_2$) to give synthesis gas (syngas) including hydrogen ($H_2$), carbon monoxide (CO), and $CO_2$, and cryogenically separating CO from the syngas giving a first stream including primarily CO and a second stream including $H_2$, CO, and $CO_2$. The method includes synthesizing methanol ($CH_3OH$) from the second stream via hydrogenation of the CO in the second stream, synthesizing dimethyl ether ($CH_3OCH_3$) from the methanol via dehydration of the methanol, and generating acetic acid from the dimethyl ether (DME), water, and the first stream, wherein generating the acetic acid includes carbonylation of the DME via CO of the first stream.

Another aspect relates to a method of producing acetic acid, including converting methane ($CH_4$) and carbon dioxide ($CO_2$) in a dry reformer vessel into hydrogen ($H_2$) and carbon monoxide (CO), discharging syngas from the dry reformer vessel via a dry-reformer discharge conduit to a cryogenic separation system including a cryogenic distillation column, wherein the syngas includes $H_2$, CO, and $CO_2$. The method includes cryogenically separating CO from the syngas via the cryogenic separation system, and discharging from the cryogenic separation system a first stream including primarily CO to a dimethyl ether (DME) carbonylation system having a DME carbonylation reactor vessel. The method includes discharging from the cryogenic separation system a second stream including $H_2$, CO, and $CO_2$ via a feed conduit to a methanol synthesis system. The methanol synthesis system has a methanol synthesis reactor that is a vessel. The method includes bypassing a portion of the syngas from the discharge conduit around the cryogenic separation system to the feed conduit, and synthesizing methanol ($CH_3OH$) from the second stream in the methanol synthesis system via hydrogenation of the CO from the second stream in the methanol synthesis reactor.

Yet another aspect relates to a system for producing acetic acid, including a dry reformer vessel to convert methane ($CH_4$) and carbon dioxide ($CO_2$) into hydrogen ($H_2$) and carbon monoxide (CO) and discharge synthesis gas (syngas) including $H_2$, CO, and $CO_2$. The system includes a cryogenic separation system to receive the syngas discharged from the dry reformer vessel and cryogenically separate CO from the syngas to discharge a first stream including primarily CO to a dimethyl ether (DME) carbonylation system operationally coupled to the cryogenic separation system and discharge a second stream including $H_2$, CO, and $CO_2$ to a methanol synthesis system comprising a methanol synthesis reactor vessel, wherein the cryogenic separation system includes a cryogenic distillation column, and wherein the DME carbonylation system includes a DME carbonylation reactor vessel. The system includes a bypass conduit to convey a portion of the syngas from the dry reformer vessel around the cryogenic separation system to the second stream. Lastly, the system includes the methanol synthesis system to form methanol ($CH_3OH$) from the second stream via hydrogenation of the CO from the second stream in the methanol-synthesis reactor vessel.

The details of one or more implementations are set forth in the accompanying drawings and the description below. Other features and advantages will be apparent from the description and drawings, and from the claims.

DETAILED DESCRIPTION

Some aspects of the present disclosure are directed to utilization of carbon dioxide to produce acetic acid. This disclosure relates to receiving carbon dioxide to produce synthetic gas (syngas) and the cryogenic processing of the syngas. Some aspects of the present disclosure are directed to acetic acid production through dimethyl ether (DME) carbonylation via cryogenic separation of syngas. In implementations, carbon monoxide (CO) produced through dry reforming is cryogenically separated from the syngas and introduced to carbonylate the DME to acetic acid. The techniques may promote carbon dioxide ($CO_2$) utilization through dry reforming that introduces raw materials for acetic acid production and that can reduce production costs and $CO_2$ emissions compared to conventional production of acetic acid.

Due to the mounting concerns about climate change, CCUS (carbon capture, utilization, and storage) is a focus of research and development around the world. The utilization can include conversion. $CO_2$ conversion technologies have attracted attention at least because of difficulties associated with geological storage of $CO_2$. An aim of $CO_2$ conversion may be to utilize concentrated $CO_2$ (e.g. from $CO_2$ capture) as a feedstock to produce valuable chemicals via various conversion processes.

In implementations herein, dry reforming of methane ($CH_4$) is a $CO_2$ conversion technology for mitigating $CO_2$ emissions. The dry reforming of methane (DRM) has relatively high $CO_2$ utilization ratio (e.g., molar ratio $CH_4$:$CO_2$=1:1) and thus may facilitate $CO_2$ reduction. Embodiments herein utilize $CO_2$ as feedstock via DRM to produce acetic acid.

As presented herein in embodiments, the syngas produced from DRM is utilized in acetic acid production. The syngas produced from DRM may be primarily hydrogen ($H_2$) and carbon monoxide (CO) at a molar ratio of 1:1 based on the ideal thermodynamic equilibrium. The syngas produced from DRM may also include $CO_2$. The acetic acid ($CH_3COOH$) produced via the syngas may be via the overall reaction $2H_2+2CO \rightarrow CH_3COOH$. This technique is different than production of acetic acid via methanol carbonylation utilizing methanol and CO as feedstock. Further, embodiments rely on CO from DRM and not CO from steam methane reforming. Embodiments via cryogenic separation of syngas produce DME and produce acetic acid through DME carbonylation. Integrated are: (1) DRM to provide manufacturing materials; and (2) acetic-acid synthesis by DME production and DME carbonylation. In support, a modeling study with the process simulator Aspen Plus® considered the present DRM-based path having DME carbonylation path. In addition, $CO_2$ lifecycle assessment (LCA) and techno-economic analysis were examined by comparison with the conventional case of methanol carbonylation to produce acetic acid.

Figure 1:
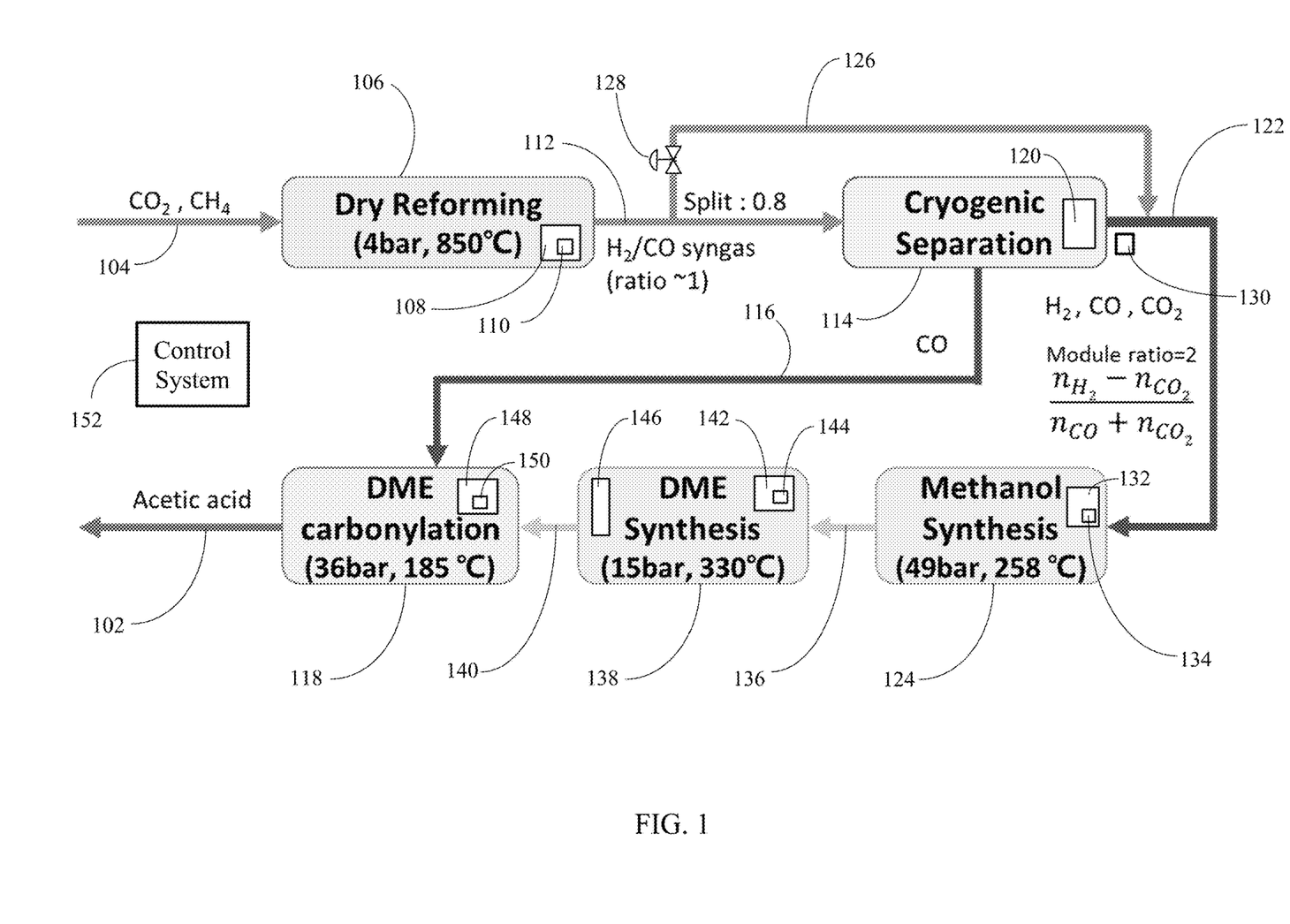
FIG. 1 is a diagram of a system that produces acetic acid.

FIG. 1 is a system 100 that produces acetic acid 102. The feed 104 includes $CO_2$ and $CH_4$. Advantageously, utilization of $CO_2$ as feed can reduce $CO_2$ emissions (the $CO_2$ footprint) at a facility. In implementations, the $CH_4$ may be fed in a methane-rich stream, such as natural gas.

A dry reforming system 106 receives the feed 104 and performs the dry reforming reaction $CO_2+CH_4\rightarrow 2H_2+2CO$. The dry reforming system 106 includes a dry reformer vessel 108 (e.g., stainless steel) having a dry reforming catalyst 110. The dry reformer vessel 108 may be, for instance, a fixed-bed reactor (e.g., multi-tubular fixed-bed reactor) having the catalyst 110 in a fixed bed. The dry reformer vessel may be a fluidized bed reactor that operates with a fluidized bed of the reforming catalyst 110. The reforming catalyst 110 may be or include, for example, noble metals, nickel (Ni), or Ni alloys. In some embodiments, the catalyst is magnesium oxide (MgO) or MgO nanoparticles. The MgO or MgO nanoparticles may be promoted with Ni and/or molybdenum (Mo), for example. Other reforming catalysts are applicable.

In operation, the dry reformer vessel 106 converts the $CH_4$ and $CO_2$ in the presence of the reforming catalyst 110 into syngas and discharges the syngas 112. The example operating conditions of the dry reformer vessel 108 in the dry reformer system 106 are depicted as 4 bar and 950° C. As used herein, bar is in absolute pressure. The operating pressure in the dry reformer vessel 108 may be, for example, in the range of 2 bar to 28 bar, or less than 30 bar. In some implementations, the operating pressure may be greater than 30 bar to provide additional motive force for flow of the discharged syngas 112 to downstream processing. The operating temperature of the dry reformer vessel 108 may be, for example, in the ranges of 500° C. to 1100° C., 600° C. to 1000° C., 700° C. to 950° C., at least 500° C., less than 1000° C., or less than 900° C. The dry reforming reaction may generally be endothermic. The dry reformer vessel 108 (dry reformer reactor vessel) may have a jacket for heat transfer and temperature control. In operation, a heat transfer fluid (heating medium) may flow through the jacket for temperature control of the dry reformer vessel 108. Heat transfer may generally occur from the heat transfer fluid in the jacket to the dry reforming reaction mixture (process side of the dry reformer vessel 108). In other embodiments, electrical heaters may provide heat for the endothermic dry reforming reaction. The electrical heaters may be disposed in the dry reformer vessel 108 or on an external surface of the dry reformer vessel 108. In yet other embodiments, the dry reformer vessel 108 may be disposed in a furnace (e.g., a direct fired heater) to receive heat from the furnace for the dry reforming reaction and for temperature control of the dry reformer vessel 108. Other configurations of heat transfer and temperature control of the dry reformer 108 are applicable.

The dry reforming of the $CH_4$ with the $CO_2$ and reforming catalyst 110 generally gives syngas 112 having $H_2$ and CO. The dry reforming reaction via the catalyst 110 in the dry reformer vessel 108 may be represented by $CH_4+CO_2\rightarrow 2H_2+2CO$. The molar ratio of $H_2$ to CO in the syngas 112 based on the ideal thermodynamic equilibrium is 1:1 but in practice can be different than 1:1. Unreacted $CH_4$ may discharge in the syngas 112 stream. In some implementations, unreacted $CH_4$ may be separated from the discharged syngas 112 and recycled to the dry reformer vessel 108. The syngas 112 may also include $CO_2$, for example, at less than 10 mole percent (mol %).

The dry reformer system 106 includes feed conduit(s) for the feed 104. The $CO_2$ and $CH_4$ (or natural gas) may be introduced in a combined stream or in separate streams to the dry reformer vessel 108. In implementations, a feed conduit may add $CO_2$ to a feed conduit conveying $CH_4$ (or natural gas) for introduction to the dry reformer vessel 108. The flow rate (e.g., volumetric rate, mass rate, or molar rate) of the feed 104 may be controlled via flow control valve(s) (disposed along respective supply conduits) or by a mechanical compressor, or a combination thereof. The ratio (e.g., molar, volumetric, or mass) of the $CH_4$ or natural gas to the $CO_2$ may be adjusted by modulating (e.g., via one or more control valves) at least one of the flow rates of the $CH_4$ (or natural gas) or the $CO_2$. The dry reformer vessel 108 has one or more inlets to receive the feed 104. The inlet(s) may be, for example, a nozzle having a flange or threaded (screwed) connection for coupling to a feed conduit conveying the feed 104 to the dry reformer vessel 108.

The dry reformer 106 system includes a discharge conduit (dry-reformer discharge conduit) for the syngas 112. The vessel 108 may have an outlet (e.g., a nozzle with a flanged or screwed connection) for the discharge of produced syngas 112 through the discharge conduit for downstream processing. The discharge conduit may extend to the cryogenic separation system 114 to convey the syngas 112 as feed to the cryogenic separation system 114. The discharge conduit may be labeled as or coupled to a cryogenic-separation feed conduit.

In implementations, steam reforming (steam methane reforming) is not employed. Instead, the above-discussed dry reforming is employed so that the discharged syngas 112 beneficially has a molar ratio of $H_2$ to CO of about 1 per the thermodynamic equilibrium. Therefore, after processing of the syngas 112 via the downstream cryogenic separation (removal) of CO from the syngas 112 for supply of the removed CO to DME carbonylation, the remaining syngas (processed syngas) discharged from the cryogenic separation may have a desired or adjustable range for the molar ratio of $H_2$ to CO for methanol synthesis.

The syngas 112 (e.g., having a molar ratio of $H_2$ to CO of about 1) is fed via the discharge conduit from the dry reforming system 106 to the cryogenic separation system 114 to separate CO 116 from the syngas 112. The syngas 112 may be pretreated to remove impurities (e.g., water) that would freeze at cryogenic temperatures. In implementations, the cryogenic separation system 114 may discharge at least two streams including a first stream and a second stream. The first stream may be the separated CO 116 discharged to a DME carbonylation system 118. The second stream may be feed 122 (including the processed syngas) discharged to a methanol synthesis system 124.

The cryogenic separation system 114 may include a refrigeration system to provide for cryogenic temperatures, such as less than −120° C. or less than −150° C. The cryogenic separation system 114 includes a mechanical gas compressor, heat exchangers, and separation columns including a cryogenic distillation column 120. The CO 116 can be separated from the syngas 112 by cooling the syngas 112 until liquefied and then distilling at component boiling temperatures. The separation columns can include a wash column, stripping column, etc.

In addition to the cryogenic distillation, unit operations can include a methane wash, partial condensation, or CO wash, and the like. The operation can be tailored to meet a desire percent purity of the CO 116. In some implementations, the cryogenic separation system 114 may be referred to as a cold box utilized for separation of CO from syngas. As mentioned, the CO 116 separated from the syngas 112 may be fed to the DME carbonylation system 118 that discharges the acetic acid 102. Operation of the DME carbonylation system 118 is discussed below.

In implementations, the amount of CO 116 removed from the syngas 112 may approximately double the molar ratio of $H_2$ to CO in the remaining syngas (processed syngas) that discharges as the second stream. In examples, the molar ratio of $H_2$ to CO in the syngas 112 discharged from the dry reforming may be about 1 (2 moles $H_2$ per 2 moles CO), and the molar ratio of $H_2$ to CO in the processed syngas (second stream) discharged from the cryogenic distillation may be about 2 (2 moles $H_2$ per 1 mole CO).

As indicated, the syngas as processed (e.g., minus the separated CO 116) discharges from the cryogenic separation system 114 as feed 122 to the methanol synthesis system 124. A bypass 126 (including bypass conduit) around the cryogenic distillation system 114 may introduce some of the syngas 112 from upstream of the cryogenic distillation system 114 into the feed 122 discharged by the cryogenic separation system 114. A purpose of the bypass 126 may be to adjust or alter the composition of the feed 122 to the methanol synthesis system 124. For instance, the molar ratio of $H_2$ to CO in the feed 122 may be adjusted, or the molar relationships among $H_2$, CO, and $CO_2$ in the feed 122 may be adjusted. The composition of the feed 122 may be adjusted to benefit or advance the methanol synthesis reaction in the methanol synthesis system 124.

In implementations, the bypass 126 conduit may route the bypass portion of the syngas 112 from the discharge conduit from the dry reformer system 106 to the conduit conveying the feed 122 downstream of the cryogen separation system 114. This conduit conveying the feed 122 may be labeled as a discharge conduit from the cryogenic separation system 114 or as a feed conduit (methanol-synthesis feed conduit) to the methanol synthesis system 124. In some implementations, the bypass 126 may include a flow control valve 128 disposed along the bypass 126 conduit. The control valve 128 may be utilized to control the amount of syngas 112 that flows through the bypass 126 conduit to bypass the cryogenic separation system 114. In the depicted implementation, 0.2 of the syngas 112 based on volume may bypass the cryogenic separation system 114 through the bypass 126 conduit. In some instances, no syngas 112 bypasses the cryogenic separation system 114 (e.g., the control valve 128 is closed). The amount of syngas 112 based on volume that bypasses the cryogenic separation system 114 can be, for example, in the range of 0.05 to 0.4 of the syngas 112.

Components of the feed 122 (with or without addition of syngas 112 via the bypass 126 conduit) may generally include at least $H_2$, CO, and $CO_2$. An online instrument 130 (e.g., gas chromatograph analyzer) may be disposed along the discharge conduit from the cryogenic separation system 114 to measure the composition of the feed 122. As indicated, this discharge conduit from the cryogenic separation system 114 may also be or couple to a feed conduit (methanol-synthesis feed conduit) to the methanol synthesis system 124. In implementations, the molar ratio of $H_2$ to CO in the feed 122 may be specified and maintained at about 2 or at least 2, which may be beneficial for the downstream methanol synthesis.

In some implementations, the relationship of $H_2$, $CO_2$, and CO in the feed 122 may controlled per the following module ratio, where η is number of moles:

$$\frac{n_{H_2} - n_{CO_2}}{n_{CO} + n_{CO_2}}$$

This module ratio may be controlled, for example, to a value of about 2 (or at least 2), which can be beneficial for the downstream methanol synthesis. In certain implementations, the set point of the control valve 128 may be adjusted to give the desired or specified value of the module ratio in the feed 122.

The methanol synthesis system 124 may receive the feed 122 from the cryogenic separation system 114. Again, the feed 122 has CO and $H_2$, and may have $CO_2$. The methanol synthesis system 124 may react the CO and $H_2$ over catalyst to produce methanol ($CH_3OH$). This methanol synthesis can be characterized as a CO hydrogenation reaction. Methanol can be produced by the hydrogenation of CO or $CO_2$ over a catalyst (e.g., Cu-based catalyst). Catalytic conversion of $H_2$ and CO into methanol can be in a gas-phase reactor. The methanol synthesis reaction can be $2H_2+CO \rightarrow CH_3OH$. Thus, a molar ratio of $H_2$ to CO of about 2 in the feed 122 may be desirable. The molar ratio of $H_2$ to CO in the feed 122 can be maintained greater than 2, such as with the aforementioned module ratio equal to about 2. In implementations, the molar ratio of $H_2$ to CO being larger than 2 in the feed 122 (and methanol synthesis reaction) may advance conversion of $CO_2$ from the feed 122 in the methanol synthesis reaction and facilitate to suppress side reactions in the methanol synthesis.

The methanol synthesis can be labeled as hydrogenation of carbon oxides ($CO_x$) to methanol. The carbon oxides ($CO_x$) are CO and $CO_2$. In addition to minor amounts of other components, the feed 122 may include ternary mixtures of $H_2+CO+CO_2$. The ternary mixtures can have different $CO_2/CO$ molar ratios and different $H_2/CO_x$ molar ratios including as specified. Such molar ratios may be maintained, for example, via the bypass 126 and/or operation of the cryogenic separation system 114.

In the illustrated embodiment, the methanol synthesis system 124 has a methanol-synthesis reactor vessel 132 that is a vessel having a catalyst 134. The reactor vessel 132 may be a gas-phase reactor. The catalyst 134 may be a copper-based catalyst. The catalyst 134 may include copper, zinc oxide (ZnO), alumina, magnesia, copper oxide (CuO), or aluminum oxide ($Al_2O_3$), or mixtures thereof. In certain implementations, the catalyst 134 is a mixture of copper and zinc oxides, supported on alumina. For instance, the catalyst 134 is Cu—ZnO—$Al_2O_3$, sometimes modified with ingredients contributing to the increase of the copper dispersion and stability. Other catalysts are applicable. The reactor vessel 132 may be a fixed-bed reactor having the catalyst 134 in a fixed bed.

The operating conditions of the methanol-synthesis reactor vessel 132 may include, for example, an operating pressure of 49 bar and a temperature of 258° C. as depicted. The operating pressure may be, for example, in a range of 30 bar to 120 bar. The operating temperature may be, for example, in a range of 220° C. to 280° C. The operating conditions may be outside of these numerical ranges. The methanol synthesis reaction $2H_2+CO \rightarrow CH_3OH$ is generally exothermic. Therefore, heat may be removed from the methanol-synthesis reactor vessel 132, such as via a heat transfer jacket, a recirculation heat exchanger, or other heat transfer system. In implementations, the heat removed may be a source of heat utilized elsewhere in the manufacturing plant or facility, such as to generate steam or electricity.

A minor amount of byproducts may be generated in the methanol synthesis. The byproducts may include, for instance, at least one of $CH_4$, methyl formate, higher alcohols, or acetone. In implementations, unreacted CO and unreacted $H_2$ discharged from the reactor vessel 132 may be recycled to the reactor vessel 132.

The final product 136 stream discharged from the reactor vessel 132 system or the methanol synthesis system 124 may include at least 70 mol % methanol. The methanol synthesis system 124 including the reactor vessel 132 may discharge the product 136 stream via a discharge conduit as feed to a DME synthesis system 138. This product 136 stream, e.g., having methanol at greater than 70 volume percent (vol %), from the methanol synthesis system 124 as feed to the DME synthesis system 138 may be primarily methanol on a volume basis.

The DME synthesis system 138 generates a product 140 stream including DME. DME, also known as methoxymethane, may generally be a colorless gas at ambient conditions. DME has the formula $CH_3OCH_3$ and may be thought of as the simplest ether. DME may also be expressed as the formula $(CH_3)_2O$ or the simplified formula expression $C_2H_6O$.

DME may be produced in the DME synthesis system 138 by the dehydration (e.g., vapor-phase dehydration) of methanol. DME can be produced through this dehydration of methanol over a catalyst (e.g., acidic catalyst). The methanol may be dehydrated over the catalyst to produce DME via the reaction $2CH_3OH \rightarrow CH_3OCH_3+H_2O$. The reaction can be implemented as catalytic dehydration of methanol in an adiabatic fixed-bed reactor. The reaction can be labeled as methanol etherification to DME. The reaction may be exothermic (e.g., slightly exothermic).

The DME synthesis system 138 includes a reactor vessel 142 (DME-synthesis reactor vessel) having a catalyst 144 for the DME synthesis from methanol. The reactor vessel 142 may be a gas-phase reactor that can be a fixed bed reactor (catalytic fixed-bed reactor having a fixed bed of the catalyst 144) or a packed bed reactor having a packed bed of the catalyst 144, and the like. As indicated, the DME may be obtained via methanol dehydration ($2CH_3OH \rightarrow CH_3OCH_3+H_2O$) in gas phase over the catalyst 144 (e.g., acid catalyst). The catalyst 144 may be a heterogeneous catalyst. The catalyst 144 may be a metal oxide catalyst (e.g., $\gamma$-$Al_2O_3$) for heterogeneous catalysis. The catalyst 144 may include, for example, silica-alumina catalyst, silica-modified alumina, $\gamma$-alumina catalyst, aluminum oxide (e.g., $\gamma$-$Al_2O_3$), zeolites, mesoporous materials, solid acids (e.g., having moderate acidity), and so on. As also indicated, the catalytic dehydration of methanol for production of DME can be an exothermic reaction. Therefore, the temperature of the reactor 142 (e.g., adiabatic reactor) (including temperature profile of the catalyst 144) in DME production may be affected by the progress of the reaction.

The operating conditions of the reactor vessel 142 for the DME synthesis reaction may be, for example, 15 bar and 330° C. The operating pressure of the reactor vessel 142 may be, for example, in the range of 10 bar to 20 bar. The operating temperature of the reactor vessel 142 may be, for example, in the range of 270° C. to 360° C. Unreacted methanol may be separated from the reactor vessel 142 discharge stream and recycled by the reactor vessel 142. The remaining portion of the discharge stream may include DME and water and forwarded as the product 140 stream to the DME carbonylation system 118. The DME synthesis system 138 may discharge the product 140 stream that is primarily DME (and can include water) to the DME carbonylation system 118 to produce acetic acid 102.

The DME synthesis system 138 may include a distillation column 146. In certain implementations, the distillation column 146 may process the discharge stream from the reactor vessel 142 to separate unreacted methanol for return to the reactor vessel 142 and give primarily DME/water as the product 140 stream to the DME carbonylation system 118.

The DME synthesis system 138 may include a series of distillation columns 146. In one implementation, the DME synthesis system 138 includes two distillation columns 146 disposed operationally in series. In that implementation, the system 138 may include the reactor vessel 142 (e.g., fixed-bed reactor) followed by a sequence of two distillation columns 146. The first distillation column 146 separates the DME product while the second distillation column 146 recovers unreacted methanol that is recycled back. In particular, the first distillation column in the series may separate DME as product via an overhead stream (or from an upper portion of the column). The bottoms stream discharged from the bottom portion of the first distillation column may be fed to the second distillation column in the series. The second distillation column may recover methanol (unreacted methanol) via an overhead stream from the second distillation column for recycle back to the reactor vessel 142. The bottom stream from the second distillation column may include water as byproduct. This water as byproduct may be fed to the DME carbonylation system 118 for the acetic-acid synthesis.

The processing of the discharge stream from the reactor vessel 142 through distillation column(s) 146 may give the product 140 stream. The DME synthesis system 138 may discharge the product 140 stream to the DME carbonylation system 118 that produces the acetic acid 102. The product 140 stream may have, for example, at least 60 mol % DME, at least 80 mol % DME, or at least 90 mol % DME.

In alternate embodiments, the methanol synthesis system 124 and the DME synthesis system 138 may be combined. This may be characterized as a direct route of DME production with the feed 122 from the cryogenic separation system 114. The methanol synthesis reactor 132 (and catalyst 134) and the DME synthesis reactor 142 (and catalyst 144) may be combined in a same vessel. The methanol synthesis reaction and DME synthesis reaction may occur in one reactor. Such may avoid or reduce methanol isolation and purification. The combined catalyst may be a tandem catalyst as a hybrid catalyst or bifunctional catalyst that supports both the methanol formation and the methanol dehydration. Thus, DME synthesis over catalyst via CO hydrogenation may be performed. Catalysts (hybrid catalysts) for "direct" synthesis of DME from the feed 122 may provide at least two functions: methanol synthesis and methanol dehydration. The catalyst may include, for example, Cu—$Al_2O_3$ catalyst (e.g., mesoporous), Cu—ZnO—$Al_2O_3$ catalyst, zeolite catalysts (e.g., ZSM-5 catalyst), or any combinations thereof. A potential drawback of the one-step DME synthesis process may be the formation of $CO_2$ as secondary product, which may be separated from the DME mixture.

The DME carbonylation system 118 receives the DME product 140 stream from the DME synthesis system 138. The DME carbonylation system may subject the DME in the product 140 stream to carbonylation via CO and hydrolysis via water ($H_2O$) to generate acetic per the reaction $CH_3OCH_3 + H_2O + 4CO \rightarrow 2CH_3COOH$. The CO may utilized for the reaction may be the CO 116 provided from the cryogenic separation system 114. The acetic-acid synthesis reaction may be performed in a reactor vessel 148 (DME-carbonylation reactor vessel) in presence of a catalyst 150 in the reactor vessel 148. The reactor vessel 148 may be a fixed-bed reactor having the catalyst 150 as a fixed bed of catalyst. The catalyst 148 may include, for example, a metal carbonyl, rhodium, rhodium metal catalyst, rhodium-based catalyst, iridium, iridium-based catalyst, iridium-containing catalyst, zeolite catalyst, or other catalyst or catalyst types. The operating conditions of the reactor vessel 148 may be, for example 36 bar and 185° C. The operating pressure of the reactor vessel 148 for the acetic-acid synthesis reaction may be, for example, in the range of 20 bar to 50 bar. The operating temperature of the reactor vessel 148 for the acetic-acid synthesis reaction may be, for example, in the range of 150° C. to 220° C. The DME carbonylation system 118 may discharge the product acetic acid 102 stream, which may be at least 90 mol % acetic acid.

The acetic-acid production system 100 may include a control system 152 that facilitates or directs operation of the system 100, such as the supply or discharge of flow streams (including flow rate) and associated control valves, control of operating temperatures and operating pressures, and control of reactors, distillation columns, and heat exchangers, and so on. The control system 152 may include a processor and memory storing code (e.g., logic, instructions, etc.) executed by the processor to perform calculations and direct operations of the system 100. The processor (hardware processor) may be one or more processors and each processor may have one or more cores. The processor(s) may include a microprocessor, central processing unit (CPU), graphic processing unit (GPU), controller card, circuit board, or other circuitry. The memory may include volatile memory (for example, cache or random access memory), nonvolatile memory (for example, hard drive, solid-state drive, or read-only memory), and firmware. The control system 152 may include a desktop computer, laptop computer, computer server, control panels, programmable logic controller (PLC), distributed computing system (DSC), controllers, actuators, or control cards. The control system 152 may be communicatively coupled to a remote computing system that performs calculations and provides direction. The control system 152 may receive user input or remote-computer input that specifies the set points of control devices or other control components in the acetic-acid production system 100. In some implementations, the control system 152 may calculate or otherwise determine set points of control devices. Some implementations may include a control room that can be a center of activity, facilitating monitoring and control of the process or facility. The control room may contain a human machine interface (HMI), which is a computer, for example, that runs specialized software to provide a user-interface for the control system. The HMI may vary by vendor and present the user with a graphical version of the remote process. There may be multiple HMI consoles or workstations, with varying degrees of access to data. The control system may also or instead employ local control (e.g., distributed controllers, local control panels, etc.) distributed in the system 100.

The amount of the bypass portion 126 flow (e.g., mass per time, volume per time, fractional amount of incoming syngas 112, etc.) may be specified and controlled such that the feed 122 has the desired or specified value for the module ratio or for the molar ratio of $H_2$ to CO, or both. In implementations, the set point of the flow control valve 128 may be manually set by a human operator to give a desired amount of bypass flow (bypass portion 126) added to the feed 122. The set point of the flow control valve 128 may be set by master controller in the control system 152 that receives feedback from the online instrument 130. Thus, in that arrangement, the flow controller for the control valve 128 may be a slave controller. In certain implementations, a human operator may input as set point for a master controller the desired composition of the feed 122. That set point may be the specified value for the molar ratio of H2 to CO. That set point may be the specified value for the module ratio. The master controller based on feedback from the online instrument 130 may adjust the set point of the flow control valve 128 to meet the set point of the master controller.

Figure 2:
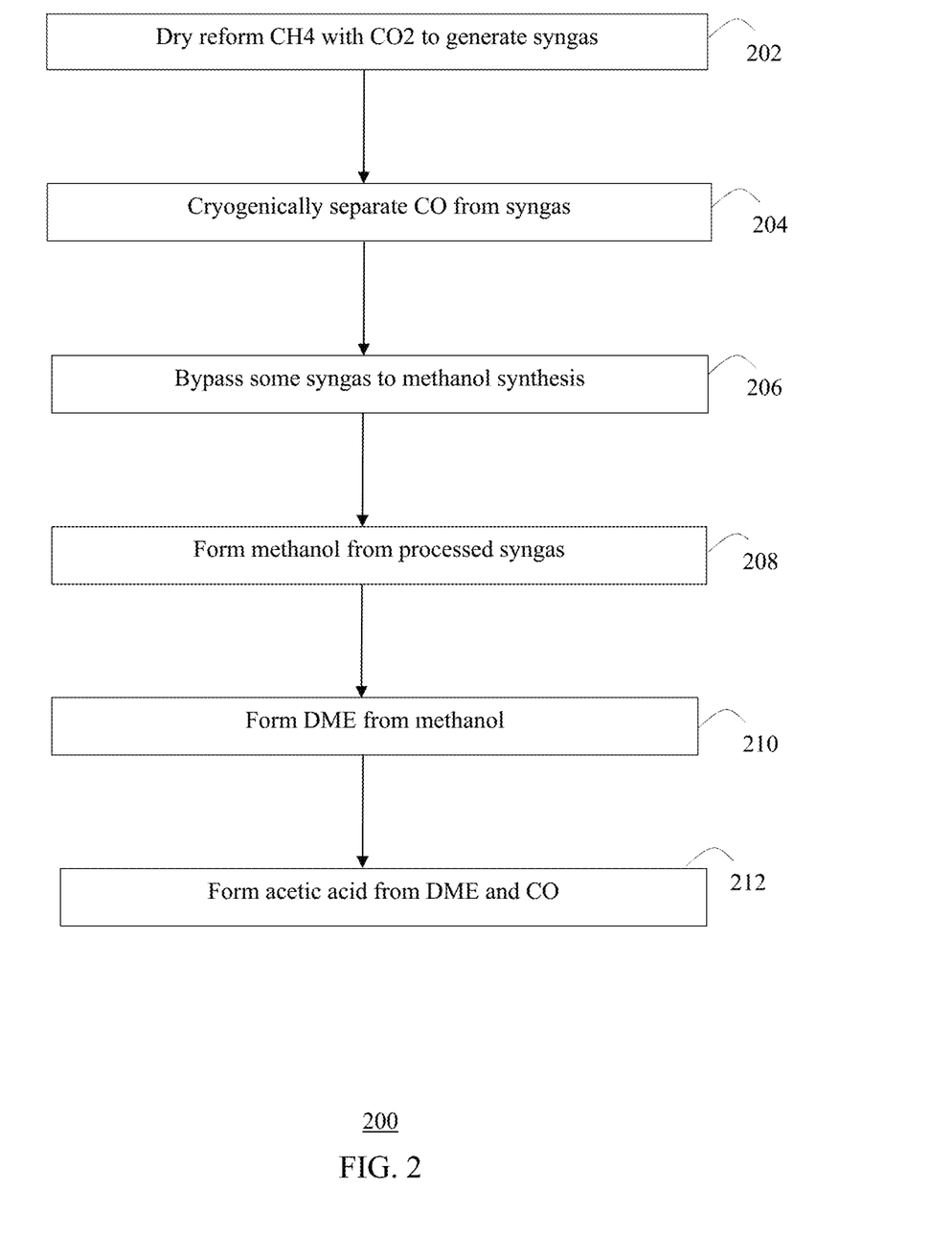
FIG. 2 is a block flow diagram of a method of producing acetic acid.

FIG. 2 is a method 200 of producing acetic acid. As indicated in the description of FIG. 1, production of acetic acid may be through carbonylation of DME utilizing CO cryogenically separated from syngas from dry reforming. The dry reforming produces syngas having molar relationship ($2H_2+2CO$) making the syngas beneficial in implementations for utilizing some of the CO for DME carbonylation, and the syngas remainder having the approximate molar relationship ($2H_2$ and $1CO$) to produce methanol. The technique cryogenically separates the CO from the syngas ($2H_2+2CO$) for the DME carbonylation and also in order to give the approximate molar relationship ($2H_2$ and $1CO$) for methanol production. Moreover, the uniqueness of dry reforming giving the approximate molar relationship ($2H_2+2CO$) is a beneficial starting point for this approach. Lastly, as discussed below, implementations may give lower final product cost and $CO_2$ footprint, as compared to conventional production methodology.

At block 202, the method 200 of embodiments of acetic-acid production herein includes dry reforming $CH_4$ with $CO_2$ to generate and give syngas including $H_2$ and CO. The syngas can also include $CO_2$. The dry reforming can involve converting $CH_4$ and $CO_2$ in a dry reformer vessel into $H_2$ and CO. The dry reforming of the methane may involve the reaction $CO_2+CH_4 \rightarrow 2H2+2CO$. Therefore, the molar ratio of $H_2$ to CO can be about 1.

At block 204, the method includes cryogenically separating CO from the syngas giving a first stream that is primarily CO and a second stream that includes $H_2$, CO, and $CO_2$. The method can include can include discharging the syngas from the dry reformer vessel via a dry-reformer discharge conduit to a cryogenic separation system that cryogenically separates the CO from the syngas. The cryogenic separation system may discharge: (a) the first stream that is primarily CO to a DME carbonylation system; and (b) the second stream (processed syngas) via a feed conduit to a methanol synthesis system. In implementations, the removal of the CO may approximately double the molar ratio of $H_2$ to CO.

At block 206, the method can include bypassing some syngas from the dry reforming around the cryogenic separation to the methanol synthesis. In particular, the method may include adding a bypass portion of the syngas to the second stream. Again, the second stream is the syngas as processed, which is syngas minus the removed CO. The bypass portion is syngas discharged from the dry reforming of the methane but that is not subjected to the cryogenically separating of the carbon monoxide. The method can include bypassing a portion of the syngas from the discharge conduit (of the dry-reformer vessel) around the cryogenic separation system to the feed conduit conveying the second stream (processed syngas) to the methanol synthesis system. In implementations, the bypass portion as a volume percent of the syngas discharged from the dry reforming may be, for example, in a range of 5% to 40%.

At block 208, the method includes forming (synthesizing) methanol from the second stream via hydrogenation of CO in the second stream. The method can include synthesizing the methanol via hydrogenation of the CO in a methanol synthesis reactor in the methanol synthesis system. The hydrogenation of the carbon monoxide may be or involve the reaction $2H_2+CO \rightarrow CH_3OH$. The second stream as feed may have a molar ratio of $H_2$ to CO of at least 2.

At block 210, the method include forming (synthesizing) DME from the methanol via dehydration of the methanol. The synthesizing of the DME via the dehydration of the methanol may be or involve the reaction $2CH_3OH \rightarrow CH_3OCH_3+H_2O$. The method can include discharging methanol from the upstream methanol synthesis system to a DME synthesis system, and synthesizing the DME via dehydration of the methanol in a DME-synthesis reactor vessel.

At block 212, the method includes forming (generating) acetic acid in the DMA carbonylation system, such as in a DMA-carbonylation reactor vessel. The method may include discharging DME from the upstream DME synthesis system to the DME carbonylation system. The acetic acid may be formed from the DME and water, as well as from the first stream (primarily CO) received from the cryogenic separation system. The generating of the acetic acid involves carbonylation of the DME via the CO provided in the first stream. The generating of the acetic acid may be or involve the reaction $CH_3OCH_3+H_2O+4CO \rightarrow 2CH_3COOH$.

The process simulator Aspen Plus® version 8.8 was utilized to model the acetic-acid production system 100 of FIG. 1 for producing acetic acid from feed including $CH_4$ and $CO_2$. The system 100 may be characterized as a DRM-based pathway for acetic acid production involving the DME carbonylation path. Example results of the simulation for costs per ton of acetic acid (AA) produced in embodiments of system 100 are given in Table 1. The costs are operational costs including the cost of feedstocks (raw materials). The currency of the costs is United States dollars ($). The numerical values for these results in Table 1 are given only as an example and not meant to limit the present techniques. The "Feed $CH_4$" is the cost for pure $CH_4$ as feed. The cost of Feed $CH_4$ can be adjusted for the feed as natural gas having the $CH_4$. The "DRM Reactor" in Table 1 is operational cost including fuel usage of DRM reactor. The dry reforming reaction is endothermic and therefore utilizes fuel. The synthesis of the methanol, synthesis of the DME, DME carbonylation, and cryogenic separation generally do not utilized fuel. The cryogenic separation may not involve a reactor. The "MEA" is monoethanolamine and may be for $CO_2$ capture unit (the MEA to facilitate removal of $CO_2$) before cryogenic separation. The MEA may be utilized for $CO_2$ scrubbing. The total cost in this example is $282 per ton of acetic acid produced.

TABLE 1

Example Results of Operating Costs

| DRM to Acetic acid | Cost($)/AA (ton) |
|---|---|
| Feed $CO_2$ | 37.8 |
| Feed $CH_4$ | 129.78 |
| Total Electricity | 84.29 |
| DRM Reactor | 13.3 |
| Total Cooling | 3.56 |
| Heating | 7.37 |
| MEA | 6.08 |
| Total | 282.18 |

For comparison, costs per ton of acetic acid produced in a methanol carbonylation system are listed below. The example total cost for the methanol carbonylation process is $400 per ton of acetic acid produced (which is greater than the $282 per ton of acetic acid produced indicated in Table 1 above). This methanol carbonylation system receives methanol and CO as feedstock and reacts the methanol with the CO to form the acetic acid. Example costs per ton of acetic acid produced in conventional methanol carbonylation are: methanol ($67.42), CO ($310.91), electricity ($4.56), and fuel ($17) for a total of $399.88 per ton of acetic acid produced.

In addition, $CO_2$ lifecycle assessment (LCA) and techno-economic analysis (TEA) were examined. LCA is methodology generally for assessing environmental impacts associated with the life cycle of a commercial product or process. TEA is generally a methodology framework involving at least process modeling and economic evaluation to analyze the technical and economic performance of a system process. An example of the $CO_2$ LCA associated with system 100 of FIG. 1 is given in Table 2. The units are kilomole per hour (kmol/hr). The "in" is the amount of received $CO_2$. The "out" is the amount of emitted $CO_2$. Based on the example parameter values in Table 2, the net $CO_2$ emission is 0.485 ton $CO_2$ per ton of acetic acid produced. Results of simulation showed 85-90% conversion of DRM feed ($CO_2$, $CH_4$). $CH_4$ was assumed as the fuel for the system process. While the study considered feeding pure $CH_4$ (not natural gas) to the DRM, the study can be adjusted without significant difference to consider feeding of natural gas having the $CH_4$. Lastly, this note fuel as $CH_4$ is for feed to the DRM reactor and not for multiple uses of fuel throughout the process. The numerical values for the results in Table 2 are given only as an example and not meant to limit the present techniques.

TABLE 2

Example of $CO_2$ Life Cycle Assessment

| kmol/hr | in | out |
|---|---|---|
| Feed $CO_2$ | 1.575 | |
| Electricity | | 0.532 |
| DRM Reactor (from fuel usage) | | 1.268 |
| NG extract transport (indirect emissions) | | 0.26 |
| Total | 1.575 | 2.06 |

For the conventional methanol-carbonylation system mentioned above to produce acetic, the $CO_2$ LCA in $CO_2$ emitted (ton) per acetic acid (ton) produced may include: methanol (0.291), CO (0.434), out $CO_2$ (0.081), reactor fuel (0.127), electricity (0.028), distillation steam (0.080), and natural gas extraction (0.029) for a total of 1.07 tons of $CO_2$ emitted per ton of acetic acid produced. This is greater than the example of 0.485 ton emitted $CO_2$ per ton of acetic acid produced that may be associated with embodiments of system 100 of FIG. 1. There is $CO_2$ emitted associated with methanol, CO, and reactor fuel. Methanol and CO are raw materials for conventional methanol carbonylation. Therefore, for during production, indirect emission of $CO_2$ associated with methanol and CO are included. Reactor fuel is related to $CH_4$ which also has an associated indirect emission of $CO_2$. That is, in natural gas (NG) extract and transport. The out $CO_2$ is $CO_2$ emission after reactor fuel is combusted.

Therefore, in view of the example values discussed above, certain acetic-acid production embodiments of the present techniques in comparison to acetic-acid production by methanol carbonylation can reduce acetic-acid production cost by about 30% while reducing the $CO_2$ emissions by about 55%. This comparison is given only as an example and not meant to limit the present techniques.

An embodiment is a system that produces acetic acid. The system may be labeled as an acetic-acid production system. The system includes a dry reformer vessel to convert $CH_4$ and $CO_2$ into $H_2$ and CO and discharge syngas including $H_2$, CO, and $CO_2$. The dry reformer vessel may convert the $CH_4$ and $CO_2$ per the reaction $CO_2+CH_4 \rightarrow 2H_2+2CO$. The system includes a cryogenic separation system to receive the syngas discharged from the dry reformer vessel and cryogenically separate CO from the syngas to discharge a first stream having primarily (greater than 50 vol %) carbon monoxide to a DME carbonylation system operationally coupled to the cryogenic separation system and discharge a second stream having $H_2$, CO, and $CO_2$ to a methanol synthesis system.

The acetic-acid production system includes a bypass conduit to convey a portion of the syngas from the dry reformer vessel around the cryogenic separation system to the second stream discharged from the cryogenic separation system. A flow control valve may be disposed along the bypass conduit to control an amount of the syngas discharged from the dry reformer vessel that bypasses around the cryogenic separation vessel to the second stream. The bypass conduit may convey the portion (bypass portion) of the syngas from a conduit conveying the syngas discharged from the dry reformer vessel. The acetic-acid production system includes the methanol synthesis system to form methanol from the second stream via hydrogenation of the CO from the second stream in the methanol-synthesis reactor vessel. The hydrogenation of the carbon monoxide may involve the reaction $2H_2+CO \rightarrow CH_3OH$.

The acetic-acid production system includes a DME synthesis system operationally coupled to the methanol synthesis system to receive methanol discharged from the methanol synthesis system and form DME via dehydration of the methanol in a DME-synthesis reactor vessel of the DME synthesis system. The dehydration of the methanol may involve the reaction $2CH_3OH \rightarrow CH_3OCH_3+H_2O$. The acetic-acid production system includes the DME carbonylation system operationally coupled to DME synthesis system to receive the DME from the DME synthesis system and form acetic acid in the DME carbonylation reactor vessel from the DME and the carbon monoxide of the first stream discharged from the cryogenic separation system. The DME synthesis system may form the acetic acid by carbonylation of the DME via the CO of the first stream in the DME carbonylation reactor per the reaction $CH_3OCH_3+H_2O+4CO \rightarrow 2CH_3COOH$.

A number of implementations have been described. Nevertheless, it will be understood that various modifications may be made without departing from the spirit and scope of the disclosure.

What is claimed is:

1. A method of producing acetic acid, comprising:
   dry reforming methane ($CH_4$) with carbon dioxide ($CO_2$) in a dry reformer vessel to give synthesis gas (syngas) comprising hydrogen ($H_2$), carbon monoxide (CO), and carbon dioxide, wherein steam reforming of methane is not performed to generate the syngas;
   receiving at a cryogenic separation system comprising a cryogenic distillation column the syngas discharged from the dry reformer vessel through a dry-reformer discharge conduit coupling the dry reformer vessel to the cryogenic separation system;
   cryogenically separating, via the cryogenic separation system, carbon monoxide from the syngas giving a first stream comprising primarily carbon monoxide and a second stream comprising hydrogen, carbon monoxide, and carbon dioxide;
   flowing a bypass portion of the syngas from the dry-reformer discharge conduit through a bypass conduit around the cryogenic separation system to a methanol-synthesis feed conduit conveying the second stream;
   controlling flow rate of the bypass portion to control in the second stream a molar relationship among $H_2$, CO, and $CO_2$, wherein controlling the flow rate comprises controlling the flow rate of the bypass portion of the syngas to the second stream with a control valve disposed along the bypass conduit, wherein the bypass portion comprises syngas discharged from the dry reforming of the methane and that is not subjected to the cryogenically separating of the carbon monoxide, and wherein the molar relationship comprises a module ratio that is $(\eta_{H2}-\eta_{CO2})/(\eta_{CO}+\eta_{CO2})$, where $\eta_{H2}$ is number of moles of hydrogen gas, $\eta_{CO2}$ is number of moles of carbon dioxide, and $\eta_{CO}$ is number of moles of carbon monoxide;
   synthesizing methanol ($CH_3OH$) from the second stream via hydrogenation of the carbon monoxide in the second stream in a methanol synthesis system comprising a methanol synthesis reactor comprising a vessel;
   synthesizing dimethyl ether ($CH_3OCH_3$) from the methanol via dehydration of the methanol; and
   generating acetic acid from the dimethyl ether (DME), water, and the first stream, wherein generating the acetic acid comprises carbonylation of the DME via carbon monoxide of the first stream.

2. The method of claim 1, wherein dry reforming the methane comprises reaction of $CO_2+CH_4 \rightarrow 2H_2+2CO$, wherein an ideal thermodynamic-equilibrium molar ratio of $H_2$ to CO of the syngas as discharged from the dry reformer vessel is 1.

3. The method of claim 1, wherein the module ratio is about 2.

4. The method of claim 1, wherein the bypass portion comprises a volume percent of the syngas discharged from the dry reformer vessel in a range of 5% to 40%.

5. The method of claim 1, comprising discharging the second stream from the cryogenic separation system through the methanol-synthesis feed conduit to the methanol synthesis system, wherein controlling flow rate of the bypass portion comprises controlling the flow rate of the bypass portion in response to composition of the second stream as measured by an online instrument disposed along the methanol-synthesis feed conduit, wherein the hydrogenation of the carbon monoxide comprises reaction of $2H_2+CO \rightarrow CH_3OH$.

6. The method of claim 1, wherein the synthesizing of the dimethyl ether (DME) via the dehydration of the methanol comprises reaction of $2CH_3OH \rightarrow CH_3OCH_3+H_2O$.

7. The method of claim 1, wherein generating the acetic acid from the dimethyl ether, water, and the first stream with carbonylation of the DME via carbon monoxide of the first stream comprises reaction of $CH_3OCH_3+H_2O+4CO \rightarrow 2CH_3COOH$.

8. A method of producing acetic acid, comprising:
converting methane ($CH_4$) and carbon dioxide ($CO_2$) in a dry reformer vessel into hydrogen ($H_2$) and carbon monoxide (CO);
discharging syngas from the dry reformer vessel via a dry-reformer discharge conduit to a cryogenic separation system comprising a cryogenic distillation column, wherein the syngas comprises hydrogen, carbon monoxide, and carbon dioxide, wherein steam reforming of methane is not performed in the dry reformer vessel, and wherein an ideal thermodynamic-equilibrium molar ratio of $H_2$ to CO of the syngas as discharged from the dry reformer vessel is 1;
cryogenically separating carbon monoxide from the syngas via the cryogenic separation system;
discharging from the cryogenic separation system a first stream comprising primarily carbon monoxide to a dimethyl ether (DME) carbonylation system comprising a DME-carbonylation reactor vessel;
discharging from the cryogenic separation system a second stream comprising hydrogen, carbon monoxide, and carbon dioxide via a methanol-synthesis feed conduit to a methanol synthesis system comprising a methanol synthesis reactor comprising a vessel;
bypassing a bypass portion of the syngas from the dry-reformer discharge conduit through a bypass conduit around the cryogenic separation system to the methanol-synthesis feed conduit;
controlling flow rate of the bypass portion to control in the second stream a molar relationship among $H_2$, CO, and $CO_2$, wherein controlling the flow rate comprises controlling the flow rate of the bypass portion of the syngas to the second stream with a control valve disposed along the bypass conduit, wherein the bypass portion comprises syngas discharged from the dry reforming of the methane and that is not subjected to the cryogenically separating of the carbon monoxide, and wherein the molar relationship comprises a module ratio that is $(\eta_{H2}-\eta_{CO2})/(\eta_{CO}+\eta_{CO2})$, where $\eta_{H2}$ is number of moles of hydrogen gas, $\eta_{CO2}$ is number of moles of carbon dioxide, and $\eta_{CO}$ is number of moles of carbon monoxide; and
synthesizing methanol ($CH_3OH$) from the second stream in the methanol synthesis system via hydrogenation of the carbon monoxide from the second stream in the methanol synthesis reactor.

9. The method of claim 8, comprising:
discharging methanol from the methanol synthesis system to a DME synthesis system comprising a DME-synthesis reactor vessel; and
synthesizing DME ($CH_3OCH_3$) from the methanol via dehydration of the methanol in the DME-synthesis reactor vessel, wherein the dehydration of the methanol comprises reaction of $2CH_3OH \rightarrow CH_3OCH_3+H_2O$.

10. The method of claim 9, wherein the module ratio is about 2.

11. The method of claim 9, comprising:
discharging DME from the DME synthesis system to the DME carbonylation system; and
generating acetic acid from the DME, water, and the first stream in the DME-carbonylation reactor vessel, wherein generating the acetic acid comprises carbonylation of the DME via carbon monoxide of the first stream.

12. The method of claim 11, wherein generating the acetic acid from the DME, water, and the first stream by carbonylation of the DME via carbon monoxide of the first stream comprises reaction of $CH_3OCH_3+H_2O+4CO \rightarrow 2CH_3COOH$.

13. The method of claim 8, wherein controlling flow rate comprises controlling the flow rate of the bypass portion in response to composition of the second stream as measured by an online instrument disposed along the methanol-synthesis feed conduit, wherein the hydrogenation of the carbon monoxide comprises reaction of $2H_2+CO \rightarrow CH_3OH$.

* * * * *

UNITED STATES PATENT AND TRADEMARK OFFICE
CERTIFICATE OF CORRECTION

| | | |
|---|---|---|
| PATENT NO. | : 12,098,122 B2 | Page 1 of 1 |
| APPLICATION NO. | : 17/206350 | |
| DATED | : September 24, 2024 | |
| INVENTOR(S) | : Ali Shakir Al Hunaidy et al. | |

It is certified that error appears in the above-identified patent and that said Letters Patent is hereby corrected as shown below:

On the Title Page

Column 2, Line 2, in Item (56) "Other Publications", please replace "Acid, """ with -- Acid," --

Column 2, Line 13, in Item (56) "Other Publications", please replace "fuels, """ with -- fuels," --

Signed and Sealed this
Twelfth Day of November, 2024

*Katherine Kelly Vidal*

Katherine Kelly Vidal
*Director of the United States Patent and Trademark Office*